(12) United States Patent
King

(10) Patent No.: US 6,316,273 B1
(45) Date of Patent: Nov. 13, 2001

(54) BIOSENSOR FOR DETECTION OF SMALL MOLECULE ANALYTES

(75) Inventor: Lionel George King, North Ryde (GB)

(73) Assignee: Australian Membrane and Biotechnology Research Institute, Chatswood (AU)

( * ) Notice: Subject to any disclaimer, the term of this patent is extended or adjusted under 35 U.S.C. 154(b) by 0 days.

(21) Appl. No.: 08/981,004

(22) PCT Filed: Jun. 20, 1996

(86) PCT No.: PCT/AU96/00368

§ 371 Date: Mar. 13, 1998

§ 102(e) Date: Mar. 13, 1998

(87) PCT Pub. No.: WO97/01091

PCT Pub. Date: Jan. 9, 1997

(30) Foreign Application Priority Data

Jun. 20, 1995 (AU) ................................................ PN 3668

(51) Int. Cl.[7] ..................... G01N 33/543; G01N 33/566; G01N 33/53; C12N 1/00
(52) U.S. Cl. ......................... 436/518; 436/527; 436/532; 435/7.2
(58) Field of Search ................................... 204/403, 415, 204/416, 418; 422/82.01, 82.02, 82.03; 435/7.2, 7.5, 817; 436/527, 518, 532

(56) References Cited

U.S. PATENT DOCUMENTS 5,436,170 * 7/1995 Cornell et al. ......................... 436/527
5,443,955 * 8/1995 Cornell et al. ........................ 435/7.21
5,874,316 * 2/1999 Cornell et al. ......................... 436/518

* cited by examiner

Primary Examiner—Prema Mertz
Assistant Examiner—Joseph F. Murphy
(74) Attorney, Agent, or Firm—Gottlieb, Rackman & Reisman, P.C.

(57) ABSTRACT

Biosensors fur use in detecting analytes, particularly small analytes such as those having a molecular weight of less than 5,000 Daltons, are disclosed which comprise a membrane and an electrode and a reservoir defined therebetween, the membrane having an inner layer proximate the electrode and an outer layer remote from the electrode comprising a closely packed array of amphiphilic molecules, a plurality or ionophores, and a plurality of membrane spanning lipids, the ionophores comprising first and second half membrane spanning monomers, the first half membrane spanning monomers being provided in the inner layer and being prevented from lateral diffusion within the membrane and the second half membrane spanning monomers being provided in the outer layer and being free to diffuse laterally within the membrane, the second half membrane spanning monomers having attached thereto a first receptor which is reactive with the small analyte, wherein a carrier to which is attached a plurality of the analyte is reversibly bound to the first receptor via the analyte. In an alternative embodiment, the second half membrane spanning monomers are attached through a carrier and/or linker group to at least one analyte, and a receptor is reversibly bound to the second half membrane spanning monomers via the analyte and said carrier and/or linker group.

42 Claims, 12 Drawing Sheets

LINKER LIPID A

LINKER GRAMICIDIN E

Figure 1A:
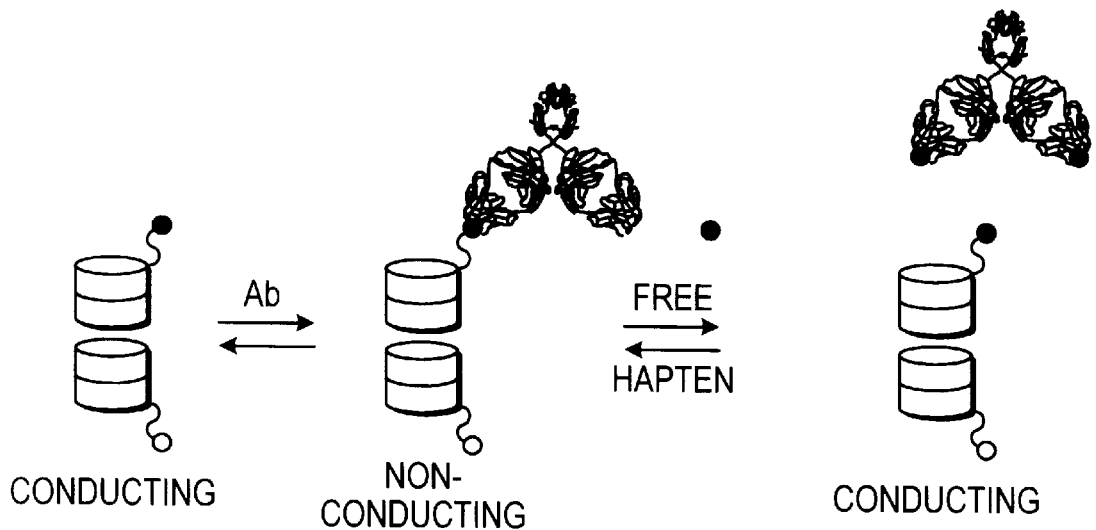

BIOTINYLATED GRAMICIDIN E
n = 1,2,3,4,5,6,7,8

DIGOXIGENIN DERIVATIVES
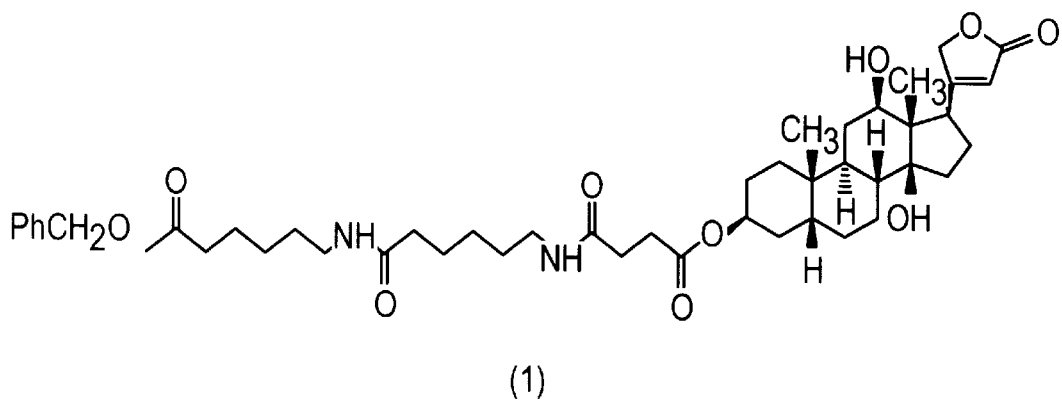
(1)
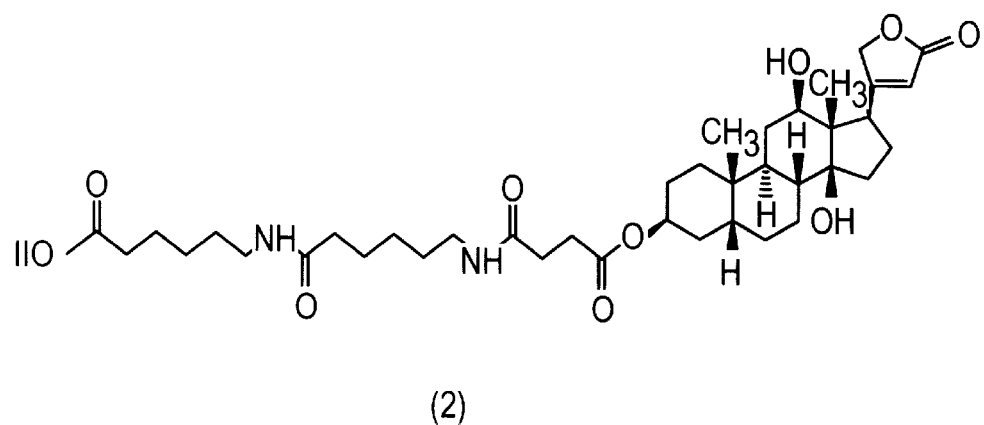
(2)
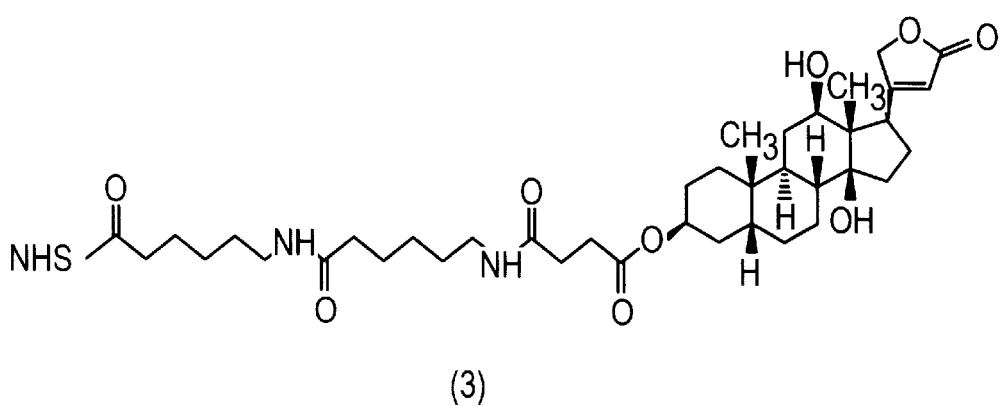
(3)
*FIG. 8*

BIOSENSOR FOR DETECTION OF SMALL MOLECULE ANALYTES

The present invention relates generally to mechanisms for modifying the electrical conductivity of ionophore containing membrane based biosensors in response to the concentration of small analytes or haptens in a sample.

Biomembranes have been constructed from a double layer of closely packed amphiphilic lipid molecules. The molecules of these bilayers exhibit the random motions characteristic of the liquid phase, in which the hydrocarbon tails of the lipid molecules have sufficient mobility to provide a soft, flexible, viscid surface. The molecules can also diffuse in two dimensions freely within their own monolayer so that two neighbouring lipids in the same monolayer exchange places with each other in a time interval several orders of magnitude less than the time for lipid molecules in opposite monolayers to exchange places.

These membrane may incorporate a class of molecules, called ionophores, which facilitate the transport of ions across these membranes. Ion channels are a particular form of ionophore, which as the term implies, are channels through which ions may pass through membranes. A favoured ionophore is gramicidin A which forms aqueous channels in the membrane. Australian Patent Specification No. 40123/85 discloses the use of membranes including ionophores in biosensors. Further examples of gated ionophores are found in Australian Patent Specification No. 21279/88, which discloses receptor molecules conjugated with a support that is remote from the receptor site. The support may be a lipid head group, a hydrocarbon chain, a cross-linkable molecule or a membrane protein or membrane polypeptide. The inner level of the membrane may be adjacent to a solid surface with groups reactive with the solid surface, and spaced from the surface to provide a reservoir region as disclosed in International Patent Specification No. 92/17788 (the disclosure of which is incorporated herein by reference).

Biosensors based on ion channels or ionophores contained within lipid membranes tethered to or deposited onto metal electrodes are disclosed in Australian Patent Specification Nos. 50334/90 and 40787/89. Those references disclose a membrane bilayer in which each layer has incorporated therein ionophores and in which the conductance of the membrane is dependent upon the presence or absence of an analyte. The disclosure of Australian Patent Specification No. 50334/94 (incorporated herein by reference) describes various ionophore gating mechanisms to modify the conductivity of the membrane in response to the presence of an analyte. In each of those gating mechanisms an inner layer of the membrane (the layer closer to the solid electrode surface, if any) contains immobilised or tethered half membrane spanning ion channels while an outer layer contains more mobile half membrane spanning ion channels. One method for immobilising the ion channels or the inner layer is to employ a polymerizable lipid layer and then cross-link the molecules of the inner monolayer and the ionophore. The conductivity of the membrane is altered by the extent to which opposing half membrane spanning ion channels align to establish a membrane spanning channel for ion transmission across the membrane.

Other biosensors based on ion channels or ionophores contained within membranes are described in International Patent Specification Nos. WO92/17788, WO93/21528, WO94/07593 and U.S. Pat. No. 5,204,239 (the disclosures of which are incorporated herein by reference). These applications also disclose methods of producing membranes with improved sensitivity using a surface amplifier effect, stability and ion flux using chemisorbed arrays of amphiphilic molecules attached to an electrode surface and means of producing lipid membranes incorporating ionophores on said chemisorbed amphiphilic molecules.

The present inventors have now developed a modified biosensor for use in the detection of small analytes. The modified biosensor can, however, also be used with larger size analytes.

Accordingly in the first aspect the present invention consists in a biosensor for use in detecting analytes, the biosensor comprising a membrane and an electrode and a reservoir defined there between, the membrane having an inner layer proximate the electrode and an outer layer remote from the electrode comprising a closely packed array of amphiphilic molecules, a plurality of ionophores, and a plurality of membrane spanning lipids, the ionophores comprising first and second half membrane spanning monomers, the first half membrane spanning monomers being provided in the inner layer and being prevented from lateral diffusion within the membrane and the second half membrane spanning monomers being provided in the outer layer and being free to diffuse laterally within the membrane, the second half membrane spanning monomers having attached thereto a first receptor which is reactive with the analyte, wherein a carrier to which is attached a plurality of the analyte is reversibly bound to the first receptor via the analyte.

In a preferred embodiment of the first aspect of the present invention, a second receptor which is also reactive with the analyte is provided on the membrane spanning lipids which are prevented from lateral diffusion in the membrane.

The first and second receptors may be the same or different.

The carrier is preferably bound, reversibly, to two or more first receptors or two or more first and second receptors, such that the carrier forms a "bridge" between the membrane members to which the receptors are attached. In this way, a portion of the second half membrane spanning monomers may be caused to locate into a position out of registration with the first half membrane spanning monomers, thereby reducing the conductivity of the membrane.

Preferably, the carrier is substantially larger than the analyte, for example 2–50 times the molecular weight of the analyte.

In a second aspect the present invention consists in a biosensor for use in detecting analytes, the biosensor comprising a membrane and an electrode and a reservoir defined there between, the membrane having an inner layer proximate the electrode and an outer layer remote from the electrode comprising a closely packed array of amphiphilic molecules, a plurality of ionophores, and a plurality of membrane spanning lipids, the ionophores comprising first and second half membrane spanning monomers, the first half membrane spanning monomers being provided in the inner layer and being prevented from lateral diffusion within the membrane and the second half membrane spanning monomers being provided in the outer layer and being free to diffuse laterally within the membrane, the second half membrane spanning monomers having attached through a carrier and/or linker group at least one analyte, wherein a receptor which is reactive with the analyte is reversibly bound to the second half membrane spanning monomers via the analyte and said carrier and/or linker group.

In a preferred embodiment the receptor has two or more analyte binding sites thereby allowing the receptor to form a bridge between two or more second half membrane spanning monomers. In this way, a portion of the second half membrane spanning monomers may be caused to aggregate, out of registration with the first half membrane spanning monomers, thereby reducing the conductivity of the membrane.

Preferably, the analyte binding sites on the receptor are separated by less than 80% of the distance between the first half membrane spanning monomers. Also, preferably, the second half membrane spanning monomer have attached through a carrier and/or linker group a plurality of the analyte.

In a further preferred embodiment of the present invention, the first receptors or, in the case of a biosensor according to the second aspect, the analyte or carrier is attached to the second half membrane spanning monomers via linker groups. Similarly, it is preferred that any second receptors are attached to the membrane spanning lipids via linker groups. Examples of suitable linker groups include protein(s) and polymers. Preferred linker groups are streptavidin, neutravidin and avidin which may be used to link biotin groups provided on the receptors and membrane members.

In a third aspect, the present invention consists in a biosensor for use in detecting analytes, the biosensor comprising a membrane and an electrode and a reservoir defined there between, the membrane having an inner layer proximate the electrode and an outer layer remote from the electrode comprising a closely packed array of amphiphilic molecules, a plurality of ionophores, and a plurality of membrane spanning lipids, the ionophores comprising first and second half membrane spanning monomers, the first half membrane spanning monomers being provided in the inner layer and being prevented from lateral diffusion within the membrane and the second half membrane spanning monomers being provided in the outer layer and being free to diffuse laterally within the membrane, the second half membrane spanning monomers being attached through a linker group to the analyte, wherein a receptor which has two or more analyte binding sites is reversibly bound to the second half membrane spanning monomers via the analyte, and wherein the membrane spanning lipids are prevented from lateral diffusion in the membrane and also have attached the analyte via a linker group.

Thus, in biosensors according to the third aspect, the receptor is able to bind to analyte attached to second half membrane spanning monomers as well as analyte attached to the membrane spanning lipids. In this way, a portion of the second half membrane spanning monomers may be caused to locate to a position out of registration with the first half membrane spanning monomers, thereby reducing the conductivity of the membrane.

In order that the nature of these aspects of the present invention may be more readily understood, preferred forms thereof are shown schematically in FIGS. 1b–1f, 2 and 3.

BRIEF DESCRIPTION OF THE ACCOMPANYING FIGURES

FIG. 1 schematically depicts various small analytes gating mechanisms for biosensors: (a) direct gating mechanism; (b) outer channel aggregation; (c) outer/inner channel lateral segregation employing free antibody; (d) outer/inner channel lateral segregation employing tethered antibody on ion channel or tethered membrane spanning lipid; (e) outer/inner channel lateral segregation employing tethered antibody on ion channel and membrane spanning lipid: and (f) depicts a preferred embodiment of the mechanism shown in (e).

FIGS. 2(a)–(d) depict alternative methods hapten attachment to membrane species.

Figure 3:
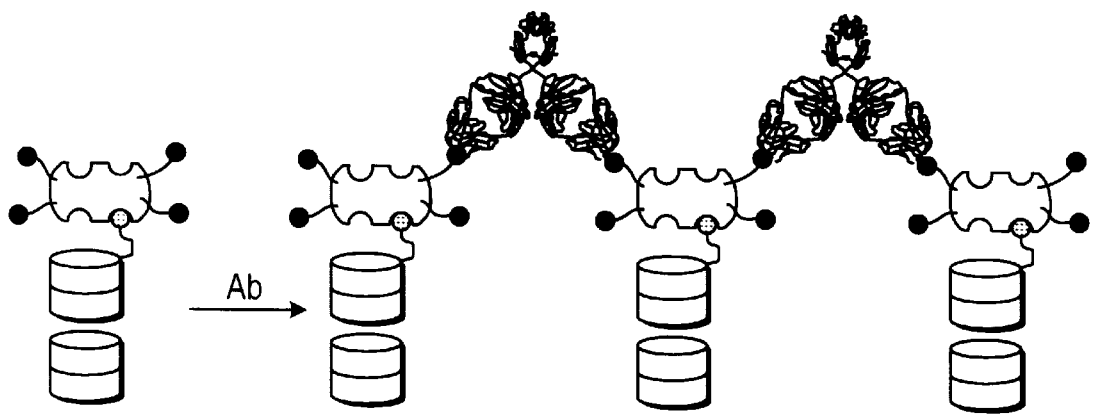

FIG. 3 depicts a method of gating by polymerisation.

Figure 4:
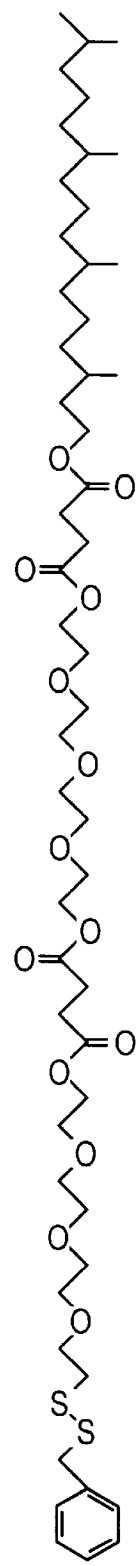

FIG. 4 provides the chemical structure of linker lipid A which may be used to construct the inner layer of the biosensor membrane.

Figure 5:
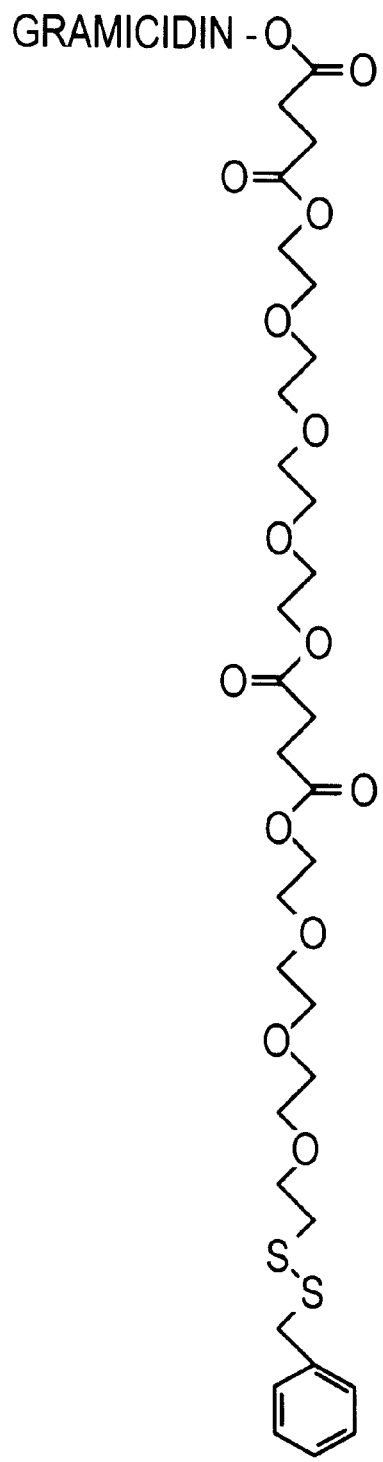

FIG. 5 provides the chemical structure of linker gramicidin B that may be used as the immobilised inner layer ion channel in biosensors of the present invention.

Figure 6:
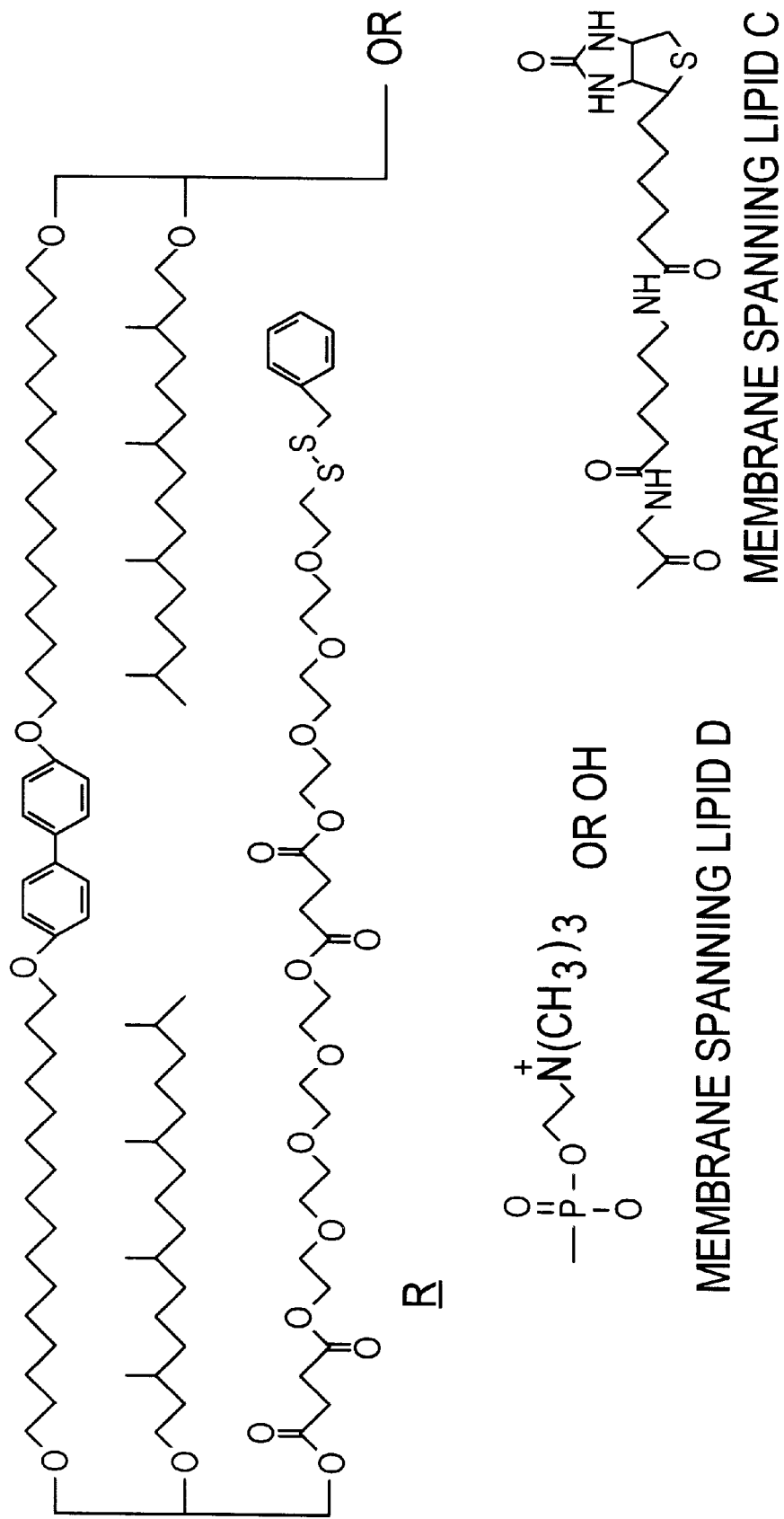

FIG. 6 provides the chemical structures of membrane spanning lipid C and D. These lipids are preferred examples of lipids suitable for constructing the inner layer of the biosensor membrane.

Figure 7:
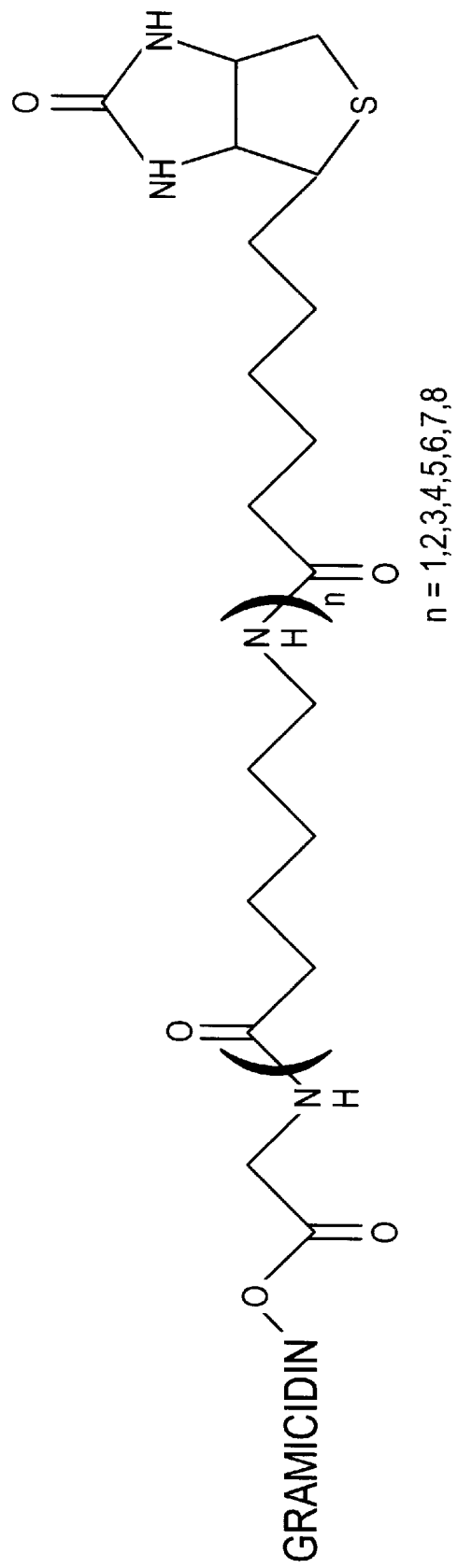

FIG. 7 provides a representation of biotinylated gramicidin E.

FIG. 8 depicts the chemical structures for various digoxigenin derivatives.

Figure 9:
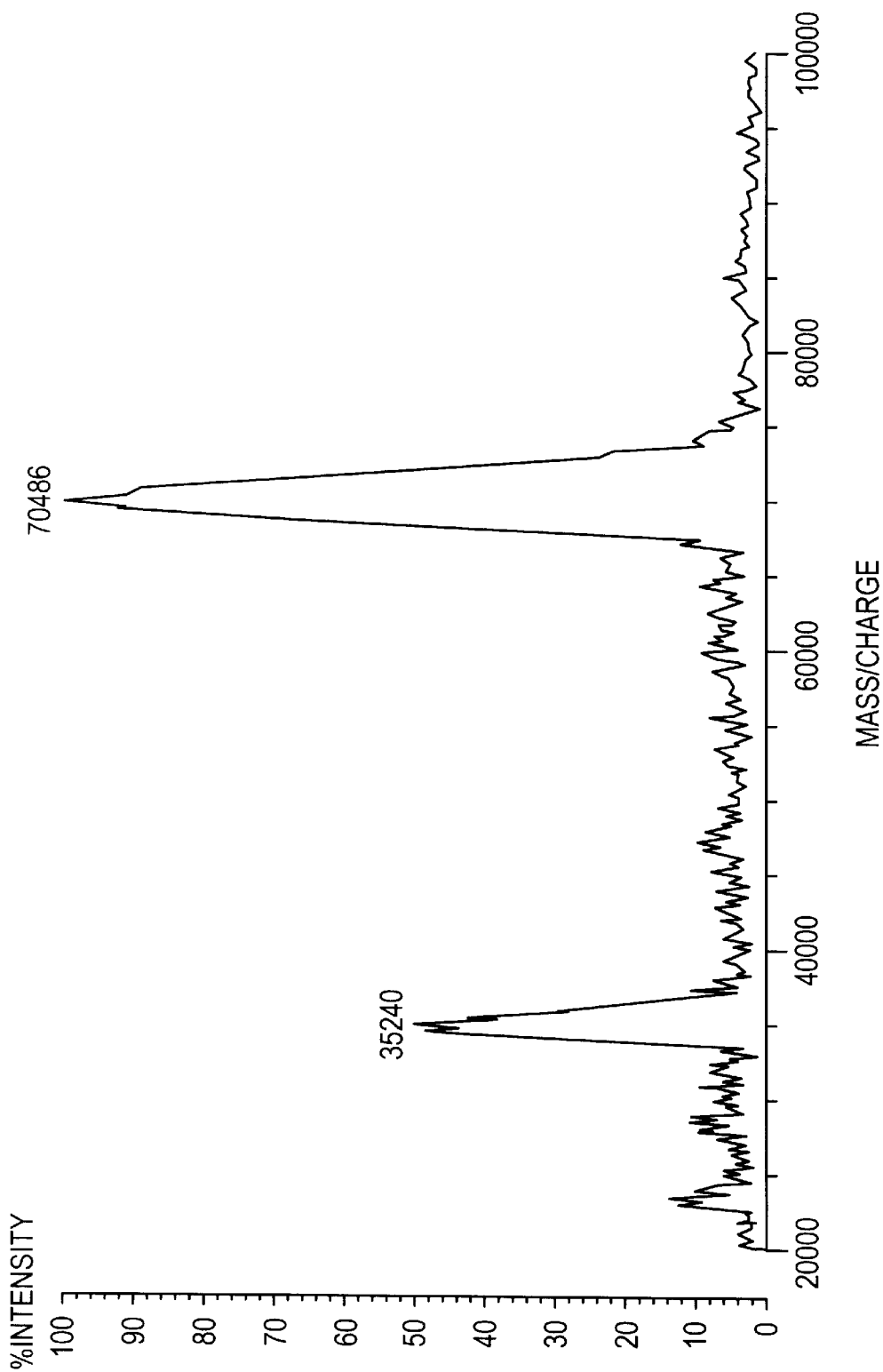

FIG. 9 provides a spectrograph obtained from a BSA-digoxigenin conjugate using MALDI (Matrix Assisted Laser Desorption Ionisation) Mass Spectroscopy.

Figure 10:
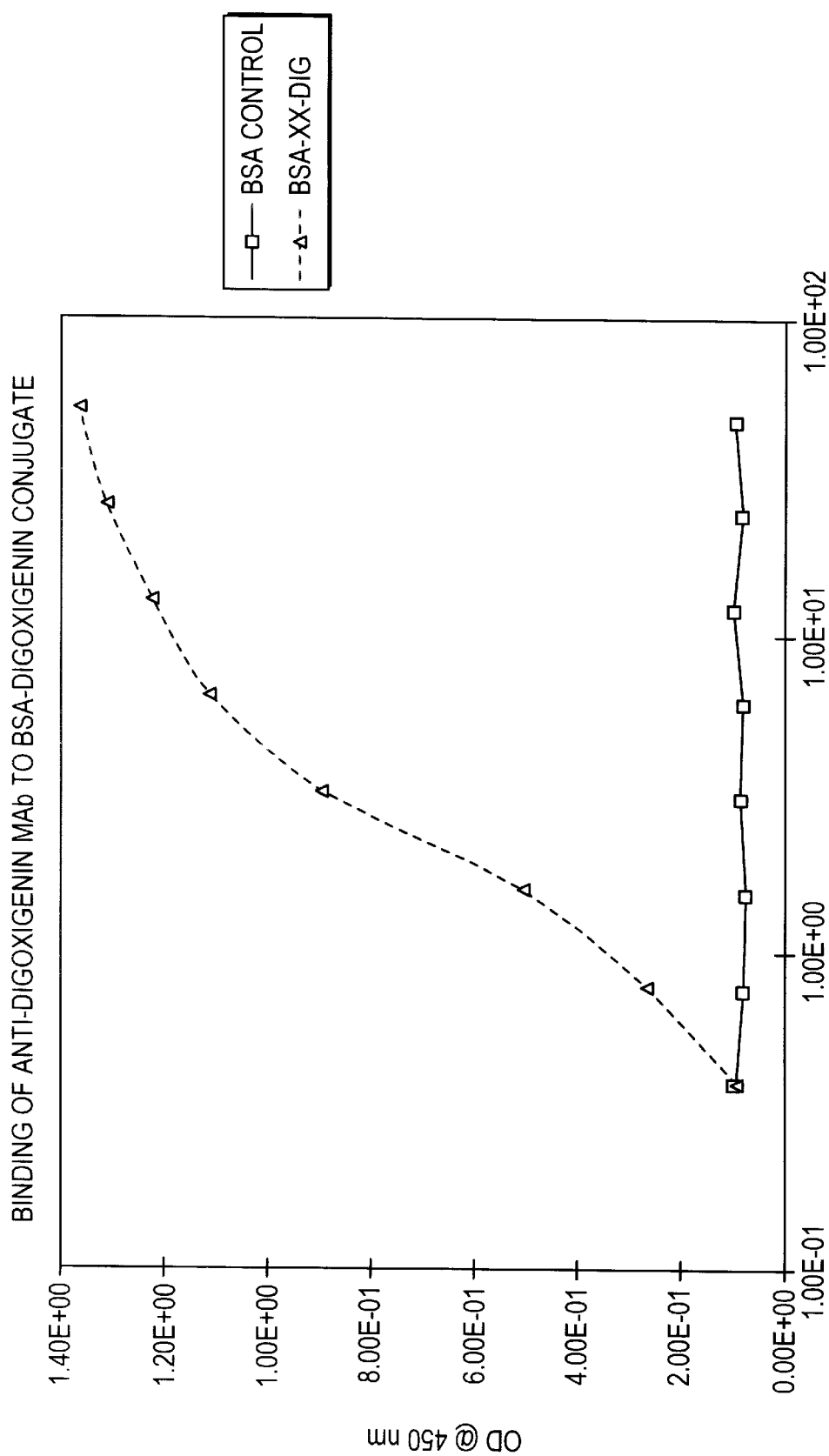

FIG. 10 provides a graph of ELISA assay results showing the immunocompetency of a BSA-digoxigenin conjugate immobilised to a microtitre plate.

In previous patents and patent applications, mechanisms have been disclosed for producing an electrical signal, dependent on the concentration of an analyte, in a biosensor based on an ion-channel containing membrane. As described above, the present invention consists in additional methods for producing such a signal, particularly in the case where the analyte is a small molecule (say, molecular weight<5000 Daltons).

Mechanisms

1. Direct Gating (FIG. 1a)

A receptor, comprising the small analyte of interest, or a derivative or analogue thereof, is attached to the mobile, outer ion channels. An antibody, a fragment thereof or another molecular species capable of recognising and binding to the small analyte of interest, is then bound to the receptor inducing a change in the ionic conductivity of the channel. When the above assembly is challenged with a medium containing the analyte of interest, the analyte competes for the antigen binding sites of the antibody or other analyte recognising species. In so doing a portion of the antibody or other analyte recognising species, which is related to the concentration of analyte in the medium being tested, is removed from the ion channel-bound receptor, returning it to its initial conducting state.

Figure 1B:
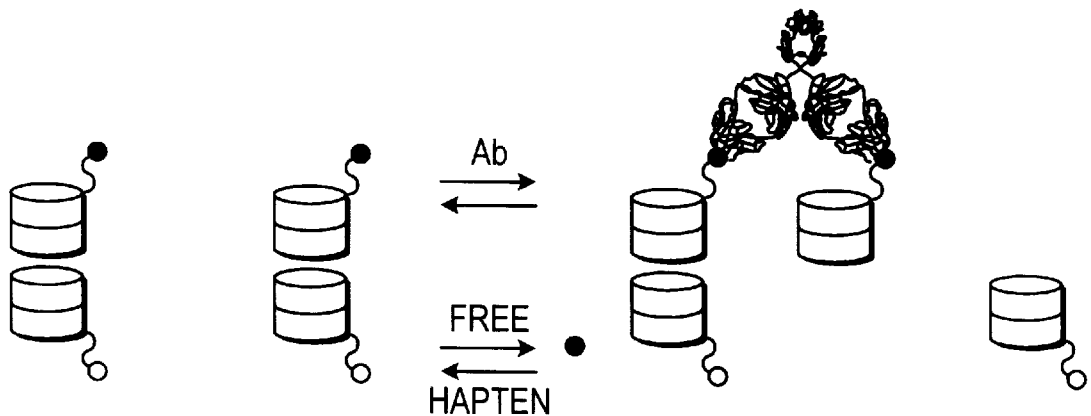

2. Outer Channel Aggregation (FIG. 1b)

A membrane is prepared with ion channels bearing receptors as described in Part 1 above. An antibody, a fragment thereof or another molecular species capable of recognising and binding to more than one copy of the small analyte of interest, is then bound to the receptor. The distance between the antigen binding sites of the antibody, or like species, must be less than (not more than 80%) the distance between the immobilised inner layer ion channels. Binding of the antibody, or like species, results in an aggregation of the outer half-membrane-spanning ion-channels, out of registration with the inner half-membrane-spanning ion channels, reducing the conductivity of the membrane. When the above assembly is challenged with a medium containing the analyte of interest, the analyte competes for the antigen binding sites of the antibody or other analyte recognising species. In so doing a portion of the antibody or other analyte recognising species, which is related to the concentration of analyte in the medium being tested, is removed from the ion channel-bound receptor, returning it to its initial conducting state.

Figure 1C:
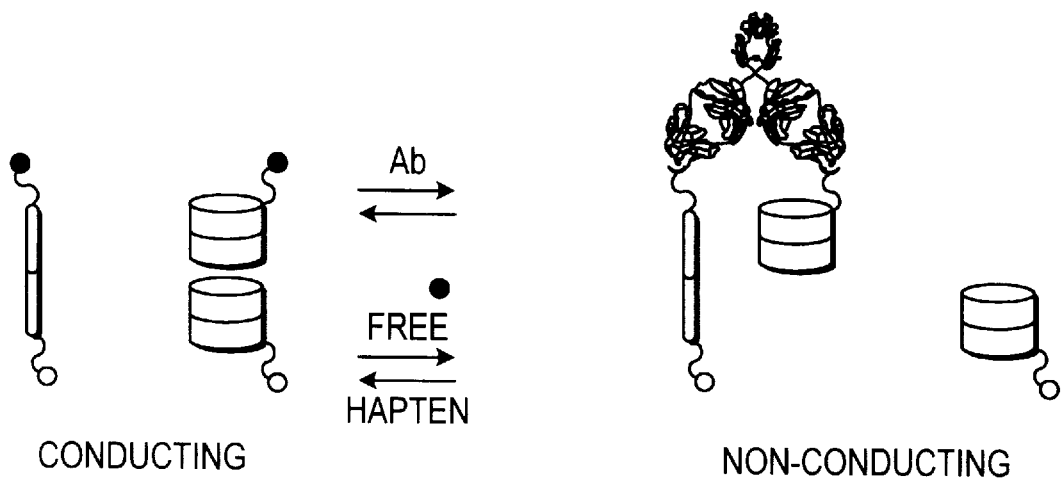

3. Outer/Inner Channel Lateral Segregation—Free Antibody (FIG. 1c)

A membrane is prepared with ion channels and membrane spanning lipids bearing receptors as described in Part 1 above. Typically, the concentration of receptor-bearing membrane spanning lipids in the membrane is much higher than that of the outer ion channels. Furthermore, the concentrations of the membrane spanning lipids and the inner ion channels are chosen such that close location of a membrane spanning lipid and an inner ion channel is a rare event. An antibody, a fragment thereof or another molecular species capable of recognising and binding to more than one copy of the small analyte of interest, is then bound to the receptors. Binding of the antibody, or like species, results in cross-linking the outer ion channels to the immobilised membrane spanning lipids, out of registration with the inner half-membrane-spanning ion channels, reducing the conductivity of the membrane. When the above assembly is challenged with a medium containing the analyte of interest, the analyte competes for the antigen binding sites of the antibody or other analyte recognising species. In so doing a portion of the antibody or other analyte recognising species, which is related to the concentration of analyte in the medium being tested, is removed from the ion channel-bound receptor, returning it to its initial conducting state.

Figure 1D:
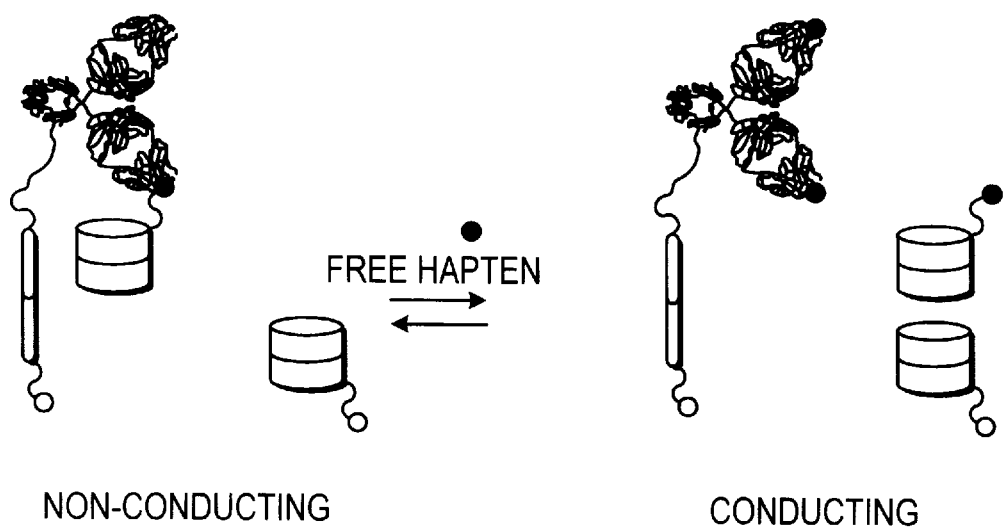

4. Outer/Inner Channel Lateral Segregation—Tethered Antibody on Ion Channel or Membrane Spanning Lipid (FIG. 1d)

A membrane is prepared with outer ion channels and membrane spanning lipids in which either the outer ion channels or membrane spanning lipids bear receptors as described in Part 1 above. An antibody, a fragment thereof or another molecular species capable of recognising and binding to the small analyte of interest, is bound to the component of outer membrane layer (ion channel or membrane spanning lipid) which does not bear the receptor. This results in cross-linking of the outer ion channels to the immobilised membrane spanning lipids, out of registration with the inner half-membrane-spanning ion channels, reducing the conductivity of the membrane. When the above assembly is challenged with a medium containing the analyte of interest, the analyte competes for the antigen binding sites of the antibody or other analyte recognising species. In so doing a portion of the outer ion channels are disconnected from the tethered membrane spanning lipids, allowing them to form membrane-spanning ion channels with the inner half-membrane-spanning ion channels and increasing the conductivity of the membrane.

Figure 1E:
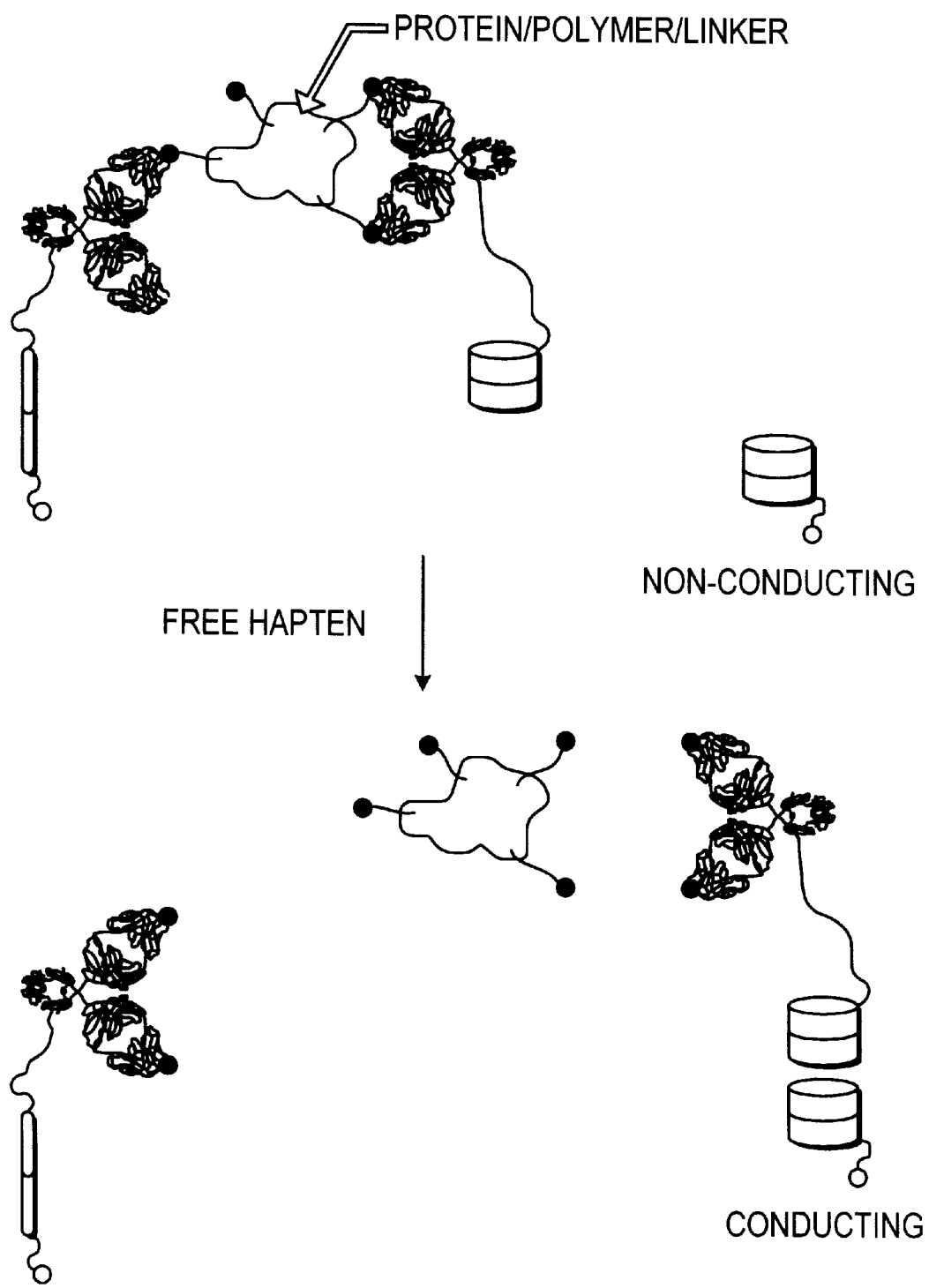
Figure 1F:
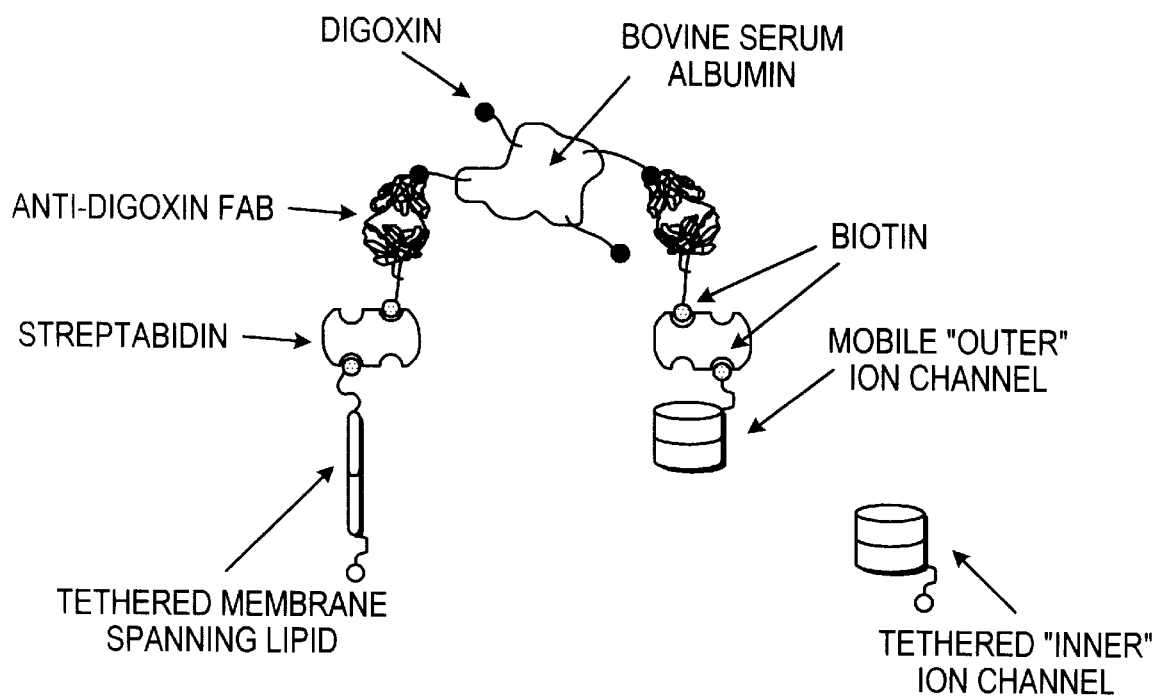

5. Outer/Inner Channel Lateral Segregation—Tethered Antibody on Ion Channel and Membrane Spanning Lipid (FIG. 1e)

A membrane is prepared with outer ion channels and membrane spanning lipids in which antibodies, fragments thereof or other molecular species capable of recognising and binding to the small analyte of interest, are bound to the outer ion channel and membrane spanning lipid. The membrane is then treated with a molecular species (e.g. protein, polymer or small organic molecule) bearing more than one copy of the small analyte of interest, or a derivative or analogue thereof. This results in cross-linking of the outer ion channels to the immobilised membrane spanning lipids, out of registration with the inner half-membrane-spanning ion channels, reducing the conductivity of the membrane. When the above assembly is challenged with a medium containing the analyte of interest, the analyte competes for the antigen binding sites of the antibody or other analyte recognising species. In so doing a portion of the outer ion channels are disconnected from the tethered membrane spanning lipids, allowing them to form membrane-spanning ion channels with the inner half-membrane-spanning ion channels and increasing the conductivity of the membrane.

In preferred embodiment of this gating mechanism, the outer half-membrane-spanning ion channels are biotinylated derivates of gramicidin and the molecular species capable of recognising and binding to the small analyte of interest is a biotinylated antibody Fab) fragment and is bound to the outer ion channels and to the biotinylated membrane spaning lipids via streptavidin, avidin or one of their modified analogues. The preferred molecular species (e.g. protein, polymer or small organic molecule) bearing more than one copy of the small analyte of interest, or a derivative or analogue thereof is the protein BSA (bovine serum albumin) functionalised with analyte analogues attached via amide bonds to BSA lysine side chain amines.

Methods of Attachment of the Receptor to the Membrane Components

Figures 2A, 2B, 2C, 2D:
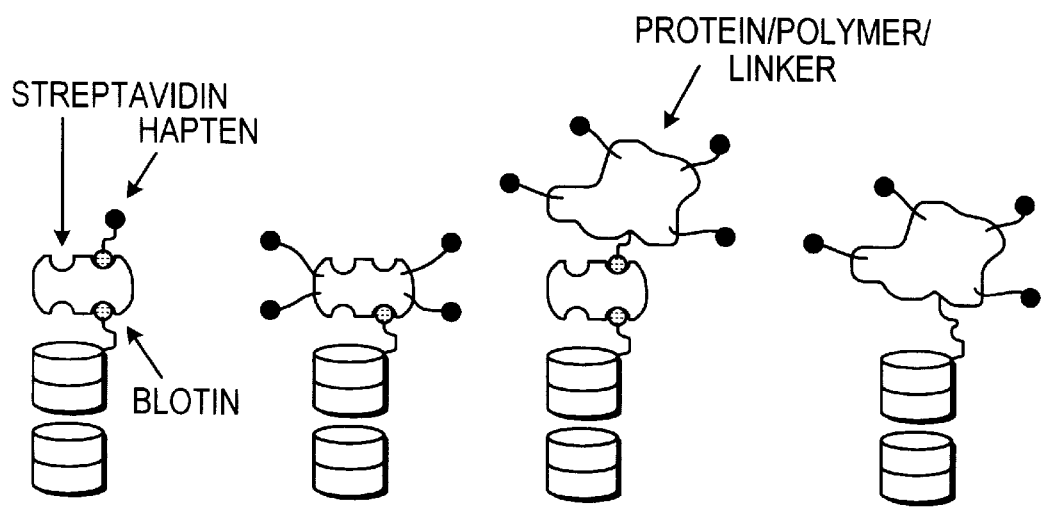

In the above examples, a small-analyte-like or antibody-like receptor must be attached to either outer ion channels, membrane spanning lipids or both. Modes of attachment for the receptor include any of those well known to the art, but particularly:

covalent attachment of a single copy of the receptor to the membrane component (ion channel or membrane spanning lipid).

covalent attachment of multiple copies of the receptor to the membrane component (FIG. 2d), including a covalent attachment of copies of the receptor to an intermediate species such as a protein (e.g. BSA), or polymer which is itself attached to the membrane component.

attachment of single (FIG. 2a) or multiple copies (FIG. 2c) of the receptor to the membrane component via a non-covalent linker e.g. providing biotin groups on the membrane component and receptor which are joined via a streptavidin or avidin molecule. As would be readily appreciated by one skilled in the art, any non-covalently associating pair of sufficient durability could be used in place of streptavidin and biotin in this role e.g. dinitrophenyl (DNP) hapten and anti-DNP antibody.

covalent attachment of the receptor to a species such as streptavidin which can then be non-covalently bound to the membrane component (FIG. 2b).

It should be noted that, in the cases where multiple copies of the small-analyte-like receptor are attached to a single outer ion channel, the possibility exists of gating by polymerisation of the ion channels on addition of an antibody-like species with two or more binding sties (FIG. 3). This represents an extended version of gating by outer channel aggregation (FIG. 1b).

EXAMPLE

Method for Construction of the Membrane

The supported bilayer for use in small analyte sensing using multimeric hapten species may be constructed as described in the co-pending international (PCT) application entitled "Self-Assembly of Sensor Membranes" filed Jun. 20, 1996.

That is, an electrode coated with a clean gold surface is contacted with a solution containing linker lipid A (FIG. 4), the disulfide of mercaptoacetic acid (maad), linker gramicidin B (FIG. 5), membrane spanning lipid C (FIG. 6) and membrane spanning lipid D, the disulfide containing components in the solution thus adsorbing onto the gold surface of the electrode. Typically the solution may contain the disulfides in the following concentrations:

| | | |
|---|---|---|
| Linker lipid A | 1 | mM |
| maad | 1 | mM |
| Linker gramicidin B | 0.0001 | mM |
| Membrane spanning lipid C | 0.0010 | mM |
| Membrane spanning lipid D dissolved in ethanol | 0.0001 | mM |

The electrode is then rinsed and the excess organic solvent used for rinsing is removed. The second layer of the lipid bilayer is then formed by adding a solution of lipid and biotinylated gramicidin E (FIG. 7), dispersed in a suitable solvent onto the electrode surface containing a first layer and rinsing the electrode surface with an aqueous solution. Typically the solution to form the second layer might contain:

| | | |
|---|---|---|
| Diphytanylphosphatidylcholine | 7 | mM |
| Glyceryl diphytanyl ether | 3 | mM |
| and biotinylated gramicidin E in ethanol | 0.0002 | mM |

To the bilayer membrane thus formed is added a solution of streptavidin, avidin, neutravidin or other avidin or streptavidin derivative (typically at a 50 μg/ml concentration for a 10 minute incubation). The electrode is then rinsed with aqueous solution in order to remove excess streptavidin, avidin, neutravidin or other avidin or streptavidin derivative, and a solution of a biotinylated receptor molecule is added (eg a biotinylated anti-hapten antibody fragment).The membrane is then rinsed and a solution containing the multi-hapten carrying species is added (typically at a concentration of 10–100 nM for 10–15 minutes). The membrane is then given a final rinse.

Requirements for the "Poly hapten Species" (i.e. Carrier Having Attached a Plurality of Analyte)

In the minimalist case, the multihapten species can be a dimer of hapten linked by a short carbon (or other) carrier chain (say, 4–50 atoms in length). Alternately, a carrier such as a protein (eg bovine serum albumin or polylysine), polysaccharide (e.g. dextran or carboxymethyl dextran) or synthetic polymer (e.g. polyacrylic acid) or copolymer can be used. It is envisaged that the use of proteins or polymers will be advantageous for providing additional solubility to haptens of sparing solubility in aqueous media. A molecular weight for a protein or polymer in the range of 10,000 to 100,000 Daltons would be expected to be optimal.

Preparation of Multi-Hapten Bovine Serum Albumin Conjugate

Preparation of Digoxigenin NHS ester (3)
(Digoxigenin derivatives illustrated in FIG. 8)

Digoxigenin-3-hemisuccinate was prepared by the method detailed in U.S. Pat. No. 3,855,208. This hemisuccinate (70 mg, 0.1426 mmol), N-hydroxysuccimimide (NHS) (98 mg, 6 equivalents), dicyclohexylcarbodiimide (DCC) (118 mg, 4 equivalents) and N,N-dimethyl-4-aminopyridine (DMAP) (18 mg, 1 equivalent) were dissolved in tetrahydrofuran (THF) (10 ml) and stirred under an atmosphere of nitrogen, overnight at room temperature.

The mixture was filtered to remove precipitated dicyclohexylurea (DCU). The filtrate was evaporated and added to N-(6-aminocaproyl)-6-aminocaproic acid benzyl ester (XXBn) (95 mg, 2 equivalents) at pH 8 in 25% MeOH/DCM (5 ml). The reaction mixture was stirred at room temperature overnight.

The mixture was evaporated and purified by silica gel chromatography on a 2×10 cm column (eluent 5% MeOH/DCM). Fractions 26–45 (5 ml fractions) contained the product and were evaporated and dried. The residue was washed with water, and dried to give (1) (68 mg).

A solution of (1) (58 mg) in MeOH (5 ml) was stirred with a catalytic amount of palladium-on-charcoal under a hydrogen atmosphere for 1 hour. The mixture was then filtered and evaporated to give the free acid (2) (50 mg).

A solution of (2) (50 mg, 0.069 mmol), DCC (43 mg, 3 equivalents) and NHS (9 mg, 5 equivalents) in dry, distilled THF (10 ml) was stirred at room temperature overnight under a nitrogen atmosphere. The mixture filtered to remove DCU and evaporated to give digoxigenin NHS ester (3). This material was used without further purification.

Synthesis of Digoxigenin Conjugates

A solution of digoxigenin NHS ester (3) in ethanol (20 mM, 4ml, 0.08 mmol) was added to a stirred solution of bovine serum albumin (BSA) (250 mg. 0.0037 mmol) dissolved in 0.05 M sodium phosphate (10 ml, pH 8.0) and 10 ml dimethylformamide (DMF). After 3 days incubation, the reaction was dialyzed in 0.05 M sodium phosphate buffer for 24 hours. The protein concentration was estimated by absorbance at 280 nm and the conjugate was stored at 4° C. The average number of haptens coupled to each BSA molecule was estimated by MALDI (Matrix Assisted Laser Desorption Ionisation) Mass Spectroscopy to be 6 digoxigenins per BSA (FIG. 9). The immunocompetency of the digoxigenin-BSA conjugate was demonstrated by ELISA assay, with the BSA-digoxigenin conjugate immobilised on the microtitre plate (FIG. 10).

DETECTION ANALYTE

The detection of analyte is achieved by addition of an analyte containing sample to the membrane assembly prepared as described above. The analyte in the sample competes with the analyte/analyte analogues on the carrier for the receptors attached to the membrane species, disconnecting the bridge between the ion channels and membrane spanning lipids. The consequence is an increase in membrane conductivity which is related to the analyte concentration in the sample.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A biosensor for use in detecting analytes, the biosensor comprising a membrane and an electrode and a reservoir defined there between, the membrane having an inner layer proximate the electrode and an outer layer remote from the electrode comprising a closely packed array of amphiphilic molecules, a plurality of ionophores, and a plurality of membrane spanning lipids, the ionophores comprising first and second half membrane spanning monomers, the first half membrane spanning monomers being provided in the inner layer and being prevented from lateral diffusion within the membrane and the second half membrane spanning monomers being provided in the outer layer and being free to diffuse laterally within the membrane, the second half membrane spanning monomers having attached thereto a first receptor which is reactive with the analyte, wherein a carrier to which is attached a plurality of the analyte is reversibly bound to the first receptor via the analyte, said analyte having a molecule weight less than 5,000 Daltons.

2. A biosensor according to claim 1, wherein the first receptors are attached to the second half membrane spanning monomers via linker groups.

3. A biosensor according to claim 2, wherein the linker groups comprise streptavidin, neutravidin or avidin.

4. A biosensor according to claim 1, wherein the carrier is bound, reversibly, to two or more first receptors such that the carrier forms a bridge between the second half membrane spanning monomers to which the first receptors are attached.

5. A biosensor according to claim 1, wherein a second receptor which is also reactive with the analyte is provided on the membrane spanning lipids which are prevented from lateral diffusion in the membrane.

6. A biosensor according to claim 1, wherein the second receptors are attached to the membrane spanning lipids via linker groups.

7. A biosensor according to claim 1, wherein the carrier is bound, reversibly, to at least one first and second receptors such that the carrier forms a bridge between the membrane members to which the first and second receptors are attached.

8. A biosensor according to claim 1, wherein the carrier is substantially larger than the analyte.

9. A biosensor according to claim 1, wherein the carrier is a protein, polysaccharide or polymer.

10. A biosensor according to claim 9, wherein the carrier is selected from bovine serum albumin, polylysine, dextran, carboxymethyldextran or polyacrylic acid.

11. A biosensor according to claim 9, wherein the carrier has a molecular weight which is 2–50 times larger than that of the analyte.

12. A biosensor according to claim 9, wherein the carrier has a molecular weight in the range of 10,000 to 100,000 Daltons.

13. A biosensor according to claim 1, wherein the receptor is an antibody.

14. A biosensor according to claim 1, wherein the second half membrane spanning monomers are gramicidin A or amphotericin B monomers.

15. A biosensor according to claim 1, wherein the analyte is digoxigenin.

16. A biosensor for use in detecting analytes, the biosensor comprising a membrane and an electrode and a reservoir defined there between, the membrane having an inner layer proximate the electrode and an outer layer remote from the electrode comprising a closely packed array of amphiphilic molecules, a plurality of ionophores, and a plurality of membrane spanning monomers, the ionophores comprising first and second half membrane spanning monomers, the first half membrane spanning monomers being provided in the inner layer and being prevented from lateral diffusion within the membrane and the second half membrane spanning monomers being provided in the outer layer and being free to diffuse laterally within the membrane, the second half membrane spanning monomers having attached through a carrier and/or linker group at least one analyte, wherein a receptor which is reactive with the analyte is reversibly bound to the second half membrane spanning monomers via the analyte and said carrier and/or linker group, said analyte having a molecule weight less than 5,000 Daltons.

17. A biosensor according to claim 16, wherein the receptor has two or mote analyte binding sites such that the receptor forms a bridge between two or more second half membrane spanning monomers.

18. A biosensor according to claim 17, wherein the analyte binding sites on the receptor are separated by less than 80% of the distance between the first half membrane spanning monomers.

19. A biosensor according to claim 16, wherein the second half membrane spanning monomers are attached through a carrier and/or linker group to a plurality of analyte.

20. A biosensor according to claim 19, wherein the plurality of the analytes is present on a carrier which is attached to the second half membrane spanning monomers.

21. A biosensor according to claim 20, wherein the carriers are attached to the second half membrane spanning monomers via linker groups.

22. A biosensor according to claim 16, wherein the analyte(s) are attached to the second half membrane spanning monomers via linker groups.

23. A biosensor according to claim 16, wherein the carrier is a protein, polysaccharide or polymer.

24. A biosensor according to claim 23, wherein the carrier is selected from bovine serum albumin, polylysine, dextran, carboxymethyldextran or polyacrylic acid.

25. A biosensor according to claim 23, wherein the carrier has a molecular weight which is 2–50 times larger than that of the analyte.

26. A biosensor according to claim 23, wherein the carrier has a molecular weight in the range of 10,000 to 100,000 Daltons.

27. A biosensor according to claim 16, wherein the first half membrane spanning monomers are gramicidin E.

28. A biosensor according to claim 16, wherein the carrier is a protein, polysaccharide or polymer.

29. A biosensor according to claim 28, wherein the carrier is selected from bovine serum albumin, polylysine, dextran, carboxymethyldextran or polyacrylic acid.

30. A biosensor according to claim 28, wherein the carrier has a molecular weight which is 2–50 times larger than that of the analyte.

31. A biosensor according to claim 28, wherein the carrier has a molecular weight in the range of 10,000 to 100,000 Daltons.

32. A biosensor according to claim 16, wherein the receptor in an antibody.

33. A biosensor according to claim 16, wherein the linker groups comprise streptavidin, neutravidin or avidin.

34. A biosensor according to claim 16, wherein the second half membrane spanning monomers are gramicidin A or amphotericin B monomers.

35. A biosensor according to claim 16, wherein the first half membrane spanning monomers are gramicidin E.

36. A biosensor according to claim 16, wherein the analyte is digoxigenin.

37. A biosensor for use in detecting analytes, the biosensor comprising a membrane and an electrode and a reservoir defined there between, the membrane having an inner layer proximate the electrode and an outer layer remote from the electrode comprising a closely packed array of amphiphilic molecules, a plurality of ionophores, and a plurality of membrane spanning lipids comprising first and second half membrane spanning monomers, the first half membrane spanning monomers being provided in the inner layer and being prevented from lateral diffusion within the membrane and the second half membrane spanning monomers being provided in the outer layer and being free to diffuse laterally within the membrane, the second half membrane spanning monomers being attached through a linker group to the analyte, wherein a receptor which has two or mote analyte binding sites is reversibly bound to the second half membrane spanning monomers via the analyte, and wherein the membrane spanning lipids are prevented from lateral diffusion in the membrane and also have attached the analyte via a linker group, said analyte having a molecule weight less than 5,000 Daltons.

38. A biosensor according to claim 37, wherein the receptor is an antibody.

39. A biosensor according to claim 37, wherein the linker groups comprise streptavidin, neutravidin or avidin.

40. A biosensor according to claim 37, wherein the second half membrane spanning monomers are gramicidin A or amphotericin B monomers.

41. A biosensor according to claim 37, wherein the first half membrane spanning monomers are gramicidin E.

42. A biosensor according to claim 37, wherein the analyte is digoxigenin.

* * * * *